US011740190B2

(12) United States Patent
Sato

(10) Patent No.: US 11,740,190 B2
(45) Date of Patent: Aug. 29, 2023

(54) X-RAY ANALYSIS DEVICE INCLUDING A SPECTROMETER TO DETECT CHARACTERISTIC X-RAYS AND RELATED X-RAY ANALYSIS METHOD

(71) Applicant: Shimadzu Corporation, Kyoto (JP)

(72) Inventor: Kenji Sato, Kyoto (JP)

(73) Assignee: Shimadzu Corporation, Kyoto (JP)

(*) Notice: Subject to any disclaimer, the term of this patent is extended or adjusted under 35 U.S.C. 154(b) by 0 days.

(21) Appl. No.: 17/188,619

(22) Filed: Mar. 1, 2021

(65) Prior Publication Data
US 2021/0372953 A1 Dec. 2, 2021

(30) Foreign Application Priority Data

May 27, 2020 (JP) .................................. 2020-092288

(51) Int. Cl.
*G01N 23/22* (2018.01)
*G01N 23/2204* (2018.01)
(Continued)

(52) U.S. Cl.
CPC ....... *G01N 23/223* (2013.01); *G01N 23/2076* (2013.01); *G01N 23/22* (2013.01);
(Continued)

(58) Field of Classification Search
CPC .............. G01N 23/2076; G01N 23/22; G01N 23/2204; G01N 23/2209; G01N 23/223; G01N 2223/076; G01N 2223/1016
(Continued)

(56) References Cited

U.S. PATENT DOCUMENTS 6,226,347 B1 * 5/2001 Golenhofen ......... G01N 23/221
378/45
6,233,307 B1 * 5/2001 Golenhofen ......... G01N 23/223
714/E11.21
(Continued)

FOREIGN PATENT DOCUMENTS

JP 2017-223638 A 12/2017

OTHER PUBLICATIONS

Adachi et al., "Development of Polychromatic Simultaneous Wavelength Dispersive X-Ray Fluorescence Spectrometer (PS-WDXRF)", Reprinted from Shimadzu Review, vol. 75, No. 3,4 (2018) pp. 85-93, submitted with a machine translation.
(Continued)

*Primary Examiner* — Allen C. Ho
(74) *Attorney, Agent, or Firm* — Muir Patent Law, PLLC

(57) ABSTRACT

Provided is an X-ray analysis device and an X-ray analysis method capable of easily analyzing a valence of a target element in a sample. A controller 22 of a signal processing device of the X-ray analysis device is provided with: a storage unit 360 for storing a calibration curve generated based on a peak energy of $K\alpha_1$ X-ray and a peak energy of $K\alpha_2$ X-ray emitted from a metal simple substance, a peak energy of $K\alpha_1$ X-ray and a peak energy of $K\alpha_2$ X-ray emitted from each of two or more types of compounds each containing the metal simple substance, and a valence of the metal in each of the two or more types of compounds; a processing unit 302 configured to acquire a peak energy of $K\alpha_1$ X-ray and a peak energy of $K\alpha_2$ X-ray of the metal emitted from the metal contained in an unknown sample; and a calculation unit 308 configured to calculate a mean valence of the metal contained in the unknown sample by applying the obtained peak energy of $K\alpha_1$ X-ray and peak energy of $K\alpha_2$ X-ray to the calibration curve.

11 Claims, 11 Drawing Sheets

(51) Int. Cl.
*G01N 23/2209* (2018.01)
*G01N 23/223* (2006.01)
*G01N 23/207* (2018.01)

(52) U.S. Cl.
CPC . *G01N 23/2209* (2018.02); *G01N 2223/0563* (2013.01); *G01N 2223/076* (2013.01); *G01N 2223/102* (2013.01); *G01N 2223/1016* (2013.01)

(58) Field of Classification Search
USPC .......................... 378/44–50, 44–50 and, 207
See application file for complete search history.

(56) References Cited

U.S. PATENT DOCUMENTS

| | | | | |
|---|---|---|---|---|
| 6,577,705 | B1* | 6/2003 | Chang | G01N 23/223 378/45 |
| 6,934,359 | B2* | 8/2005 | Chen | G21K 1/06 378/45 |
| 7,046,760 | B2* | 5/2006 | Kim | H01L 22/14 257/E21.531 |
| 7,092,843 | B2* | 8/2006 | Moore | H03M 7/30 702/179 |
| 7,187,751 | B2* | 3/2007 | Kawahara | G01N 23/223 378/45 |
| 7,450,685 | B2* | 11/2008 | Kataoka | G01N 23/2209 378/50 |
| 7,579,591 | B2* | 8/2009 | Takakura | G01N 23/2252 250/306 |
| 7,949,093 | B2* | 5/2011 | Kataoka | G01N 23/223 378/45 |
| 7,991,109 | B2* | 8/2011 | Golenhofen | G01N 23/2206 378/46 |
| 9,031,187 | B2* | 5/2015 | Yellepeddi | G01N 23/223 378/81 |
| 9,448,191 | B2* | 9/2016 | Utaka | G01N 23/223 |
| 10,256,002 | B2* | 4/2019 | Chen | G01N 23/223 |
| 10,302,579 | B2* | 5/2019 | Omote | G01N 23/2076 |
| 10,527,600 | B2* | 1/2020 | Warner | G01N 33/1813 |
| 10,578,566 | B2* | 3/2020 | Yun | G01N 23/2209 |
| 10,746,675 | B2* | 8/2020 | Mori | G06T 11/206 |
| 10,948,434 | B2* | 3/2021 | Sato | G01N 23/2076 |
| 11,112,371 | B2* | 9/2021 | Sato | G01N 23/22 |
| 11,125,704 | B2* | 9/2021 | Aoki | G01J 4/04 |
| 11,137,360 | B2* | 10/2021 | Sato | G01N 23/2076 |
| 11,199,513 | B2* | 12/2021 | Koskinen | G01T 1/2023 |
| 11,360,036 | B2* | 6/2022 | Koskinen | G21K 1/06 |
| 11,378,530 | B2* | 7/2022 | Sato | G01N 23/2209 |
| 11,435,303 | B2* | 9/2022 | Sakamae | G01N 23/2209 |
| 11,471,119 | B2* | 10/2022 | Sato | G01N 23/2206 |
| 11,609,191 | B2* | 3/2023 | Tsukamoto | G01N 23/2209 |
| 2017/0160213 | A1 | 6/2017 | Sato et al. | |

OTHER PUBLICATIONS

Ito et al., "In situ X-ray absorption spectroscopic study of Li-rich layered cathode material Li[Ni0.17Li0.2Co0.07Mn0.56]O2", Journal of Power Sources, 196 (2011) pp. 6828-6834.

Sato et al., "Polychromatic simultaneous WDXRF for chemical state analysis using laboratory X-ray source", X-Ray Spectrometry, 2017, 46, pp. 330-335.

Harada et al., "Factors Causing Intensity Changes in K Emission Spectra of Lanthanide Compounds-Feasibility for Chemical Speciation", Advances in X-Ray Chemical Analysis 34, Oct. 28, 2002, pp. 195-206, submitted with a machine translation.

Sato et al., "Evaluation of Analytical Precision of Polychromatic Simultaneous WDXRF Spectrometer and Application to Valence Analysis of Cathode Materials of Lithium-Ion Batteries", ACS Analytical Chemistry, 2020, 92, pp. 758-765.

Japanese Office Action for corresponding patent application No. JP 2020-092288 dated Jun. 20, 2023.

* cited by examiner

FIG. 6

| | Valence | $K\alpha_1$ peak energy | $K\alpha_2$ peak energy | $K\alpha_1 - nK\alpha_2$ |
|---|---|---|---|---|
| Simple metal | 0 | m1 | m2 | m1−n·m2 |
| 1st metal compound | v | a1 | a2 | a1−n·a2 |
| 2nd metal compound | w | b1 | b2 | b1−n·b2 |

FIG. 8

| | y (valence) | $K\alpha_1$ peak energy | $K\alpha_2$ peak energy | $x(K\alpha_1-nK\alpha_2)$ |
|---|---|---|---|---|
| Fe (simple metal) | 0 | 6403.719 | 6390.864 | 1250.206 |
| $Fe_3O_4$ (1st metal compound) | 2.6667 | 6403.793 | 6390.731 | 1250.387 |
| $Fe_2O_3$ (2nd metal compound) | 3.0000 | 6403.780 | 6390.687 | 1250.409 |

FIG. 13
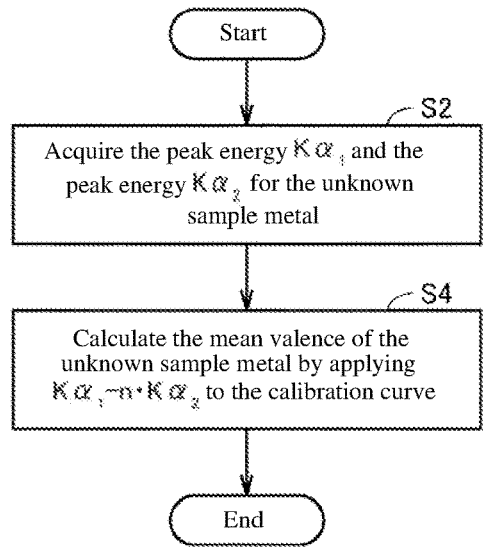
FIG. 14
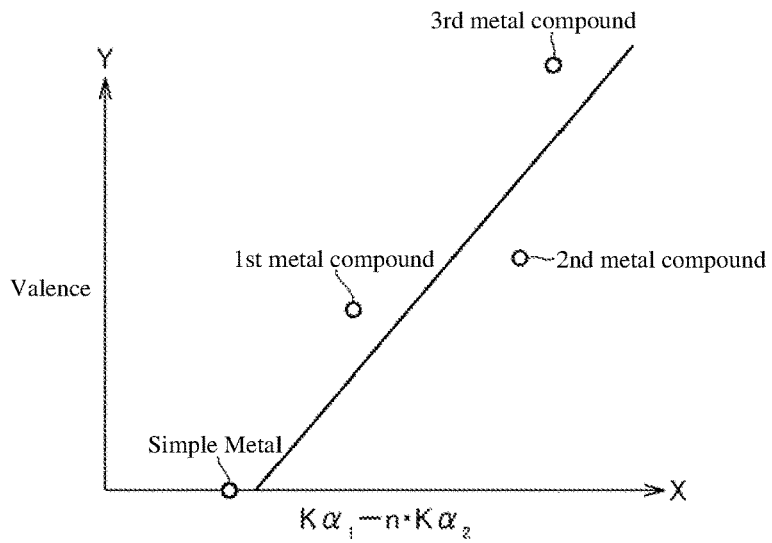
FIG. 15
|   | j |   |   |   |   |   |   |   |
|---|---|---|---|---|---|---|---|---|
|   |   | 0 | 1 | 2 | 3 | 4 | 5 | 6 | 7 |
| i | 0 |   |   |   | 5 | 1.67 | 1 | 0.71 | 0.56 |
|   | 1 |   |   |   | 3 | 1 | 0.6 | 0.43 | 0.33 |
|   | 2 |   |   |   | 1 | 0.33 | 0.2 | 0.14 | 0.11 |
|   | 3 |   |   |   |   |   |   |   |   |
|   | 4 |   |   |   |   |   |   |   |   |
|   | 5 |   |   |   |   |   |   |   |   |
|   | 6 |   |   |   |   |   |   |   |   |
|   | 7 |   |   |   |   |   |   |   |   |

FIG. 16

|   | j |   |   |   |   |   |   |   |
|---|---|---|---|---|---|---|---|---|
| i | 0 | 1 | 2 | 3 | 4 | 5 | 6 | 7 |
| 0 |   |   |   | 5 | 1.67 | 1 | 0.71 | 0.56 |
| 1 |   |   |   | 3 | 1 | 0.6 | 0.43 | 0.33 |
| 2 |   |   |   | 1 | 0.33 | 0.2 | 0.14 | 0.11 |
| 3 |   |   |   |   |   |   |   |   |
| 4 |   |   |   |   |   |   |   |   |
| 5 |   |   |   |   |   |   |   |   |
| 6 |   |   |   |   |   |   |   |   |
| 7 |   |   |   |   |   |   |   |   |

X-RAY ANALYSIS DEVICE INCLUDING A SPECTROMETER TO DETECT CHARACTERISTIC X-RAYS AND RELATED X-RAY ANALYSIS METHOD

CROSS-REFERENCE TO RELATED APPLICATIONS

This application claims priority under 35 U.S.C. § 119 to Japanese Patent Application No. 2020-092288 filed on May 27, 2020, the entire disclosure of which is incorporated herein by reference in its entirety.

BACKGROUND OF THE INVENTION

Field of the Invention

The present disclosures relates to an X-ray analysis device and an X-ray analysis method.

Background of the Invention

An X-ray analysis device for determining a valence of a sample by irradiating the sample with excitation ray is known. Characteristic X-rays emitted by the sample irradiated with the excitation ray have a wavelength determined by the atomic contained in the sample. Therefore, the X-ray analysis device can determine the valence of the sample by detecting the intensity per wavelength of the characteristic X-rays.

An atomic has a plurality of electron shells (such as a K-shell, an L-shell, and an M-shell), and when an atom contained in a sample is irradiated with X-rays, electrons of an inner core are excited by the energies of the X-rays. To an emptied shell (e.g., K-shell) caused by the excitation of the electrons, electrons are transferred from the outer shell (e.g., L-shell). The characteristic X-rays generated by the transition of electrons from the L-shell to the K-shell is called Kα X-ray, and the characteristic X-rays generated by the transition of electrons from the M-shell to the K-shell is called Kβ X-ray.

Non-Patent Document 1 described below discloses an X-ray analysis device for detecting a valence of a sample based on a peak energy of Kβ X-ray. In this X-ray analysis device, a calibration curve indicating the relation between the peak energy of Kβ X-ray and a valence is generated, and a mean valence of a sample is detected based on this calibration curve.

PRIOR ART DOCUMENTS

Non-Patent Document

Non-Patent Document 1: Adachi, and five others, "Developing Simultaneous Multiple Wavelength Dispersive Fluorescent X-Ray Analysis Device (PS-WDXRF)," Shimadzu commentary, Volume 75, Vol. 3 and 4, 2018

SUMMARY OF THE INVENTION

Problems to be Solved by the Invention

Incidentally, it may be desired to measure a mean valence of a metal (Fe) in a sample in which a metal simple substance (e.g., Fe) and a compound containing the metal (e.g., $Fe_2O$) are mixed. Note that the valence of Fe which is a metal simple substance is "0", and the valence of Fe of $Fe_2O_3$ which is a composition is "3". In a sample, in a case where the ratio of Fe to $Fe_2O_3$ is, for example, 1:2, the mean valence of the metal (Fe) is calculated by $(0\times\frac{1}{3})+(3\times\frac{2}{3})$, and becomes "2".

Thus, although the valence of a metal simple substance (e.g., Fe) is 0, when a sample of a metal simple substance is measured with the X-ray analysis device described in Non-Patent Document 1, a mean valence that differs from 0 is detected. Therefore, when a mean valence is calculated by the X-ray analysis device described in Non-Patent Document 1 for a sample containing a metal simple substance, there is a problem that a mean valence different from an actual mean valence may be calculated.

The present invention has been made to solve such problems, and an object thereof is to provide an X-ray analysis device and an X-ray analysis method capable of improving the accuracy of calculating a mean valence of a metal in a sample.

Means for Solving the Problem

An X-ray analysis device according to the present disclosure includes:
a device body provided with a spectrometer, the spectrometer being configured to detect intensity of characteristic X-rays for each wavelength by dispersing the characteristic X-rays generated by a sample irradiated with excitation ray; and
a signal processing device configured to process a signal output from the device body,
wherein the signal processing device includes:
a storage unit configured to store a calibration curve, the calibration curve being generated based on
a peak energy of $K\alpha_1$ X-ray and a peak energy of $K\alpha_2$ X-ray emitted from a metal simple substance,
each of a peak energy of $K\alpha_1$ X-ray and a peak energy of $K\alpha_2$ X-ray emitted from two or more types of compounds each containing the metal in their compositions, the compounds being different in a valence of the metal, and
a valence of the metal in each of the two or more types of compounds; and
an operation unit configured to acquire a peak energy of the $K\alpha_1$ X-ray emitted from the metal contained in an unknown sample and a peak energy of the $K\alpha_2$ X-ray emitted from the metal based on intensity of the peak energy for each wavelength detected by the device body, and calculate a mean valence of the metal contained in the unknown sample by applying the acquired peak energy of the $K\alpha_1$ X-ray and the peak energy of the $K\alpha_2$ X-ray to the calibration curve.

Effects of the Invention

According to the present disclosure, it is possible to provide an X-ray analysis device and an X-ray analysis method capable of improving calculation accuracy of a mean valence of a metal in a sample.

BRIEF DESCRIPTION OF THE DRAWINGS

The preferred embodiments of the present invention are shown by way of example, and not limitation, in the accompanying figures.

FIG. 6 shows symbols of the valence, the peak energy of the $K\alpha_1$ X-ray, and the peak energy of the $K\alpha_2$ X-ray in each of $Fe_2O_3$, $Fe_3O_4$, and Fe.

FIG. 8 is a diagram showing specific values of the valence, the peak energy of the $K\alpha_1$ X-ray, and the peak energy of the $K\alpha_2$ X-ray in each of $Fe_2O_3$, $Fe_3O_4$, and Fe.

FIG. 13 is an example of a flowchart showing a method of calculating a mean valence.

FIG. 14 is a diagram showing a calibration curve generated by the least-squares method.

FIG. 15 is a diagram showing all possible composition ratios of the first substance to the second substance in a tabular form.

FIG. 16 is a diagram showing a display mode of the determined composition ratio.

EMBODIMENTS FOR CARRYING OUT THE INVENTION

Figure 1:
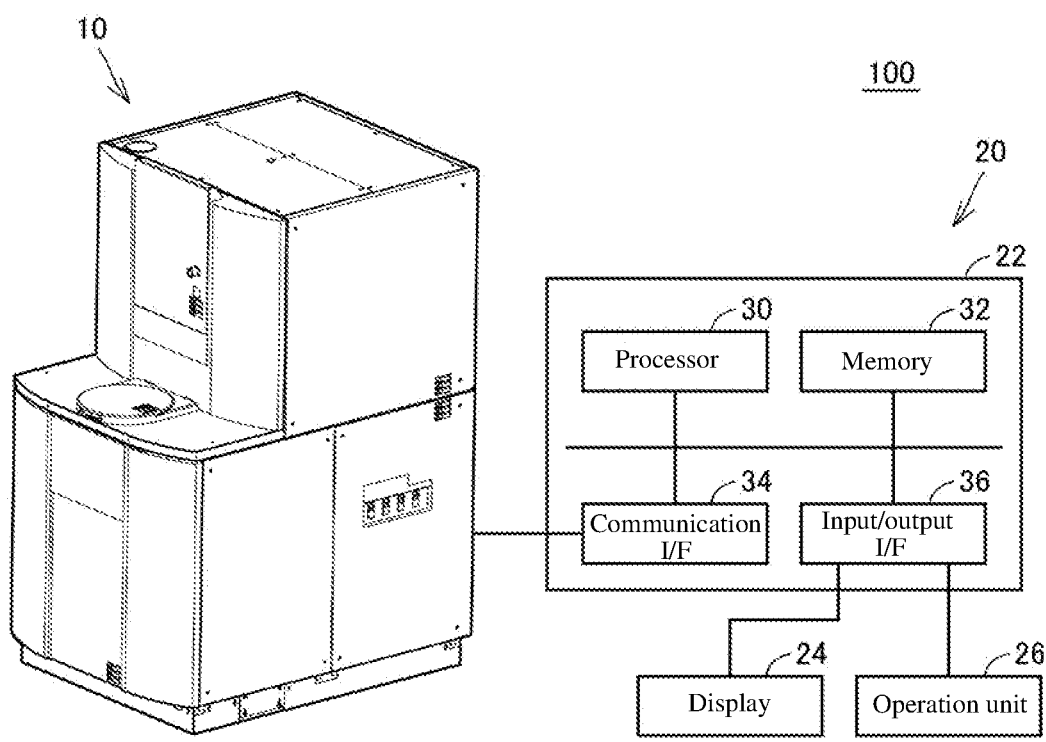
FIG. 1 is a schematic configuration diagram of an analysis device 100 according to this embodiment.

Hereinafter, some embodiments of the present invention will be described in detail with reference to the attached drawings. The same or corresponding portion in the drawing is denoted by the same reference numeral, and the description thereof will not be repeated.

<Configuration of X-Ray Analysis Device>

The X-ray analysis device according to this embodiment is an X-ray analysis device provided with a wavelength dispersive spectrometer. Hereinafter, a wavelength dispersive type fluorescent X-ray analysis device will be described as an example of the X-ray analysis device according to this embodiment. The "wavelength dispersive type" fluorescent X-ray analysis device is a system to detect a characteristic X-ray spectrum by measuring the characteristic X-ray intensity for each target wavelength by dispersing the characteristic X-rays by a spectroscopic element.

FIG. 1 is a schematic configuration diagram of a wavelength dispersive type fluorescent X-ray analysis device (hereinafter also referred to as "analysis device 100") according to this embodiment. Referring to FIG. 1, the analysis device 100 is provided with a device body 10 and a signal processing device 20.

The device body 10 is configured to emit excitation ray to a sample and detect characteristic X-rays generated from the sample. The excitation ray is typically X-rays. The characteristic X-rays and fluorescent X-rays are synonymous. The detection signal corresponding to the characteristic X-rays detected by the device body 10 is transmitted to the signal processing device 20.

The signal processing device 20 is provided with a controller 22, a display 24, and an operation unit 26. The signal processing device 20 controls the operation of the device body 10. Further, the signal processing device 20 is configured to process the detection signal transmitted from the device body 10, and displays the results based on the analysis on the display 24. To the controller 22, the display 24 and the operation unit 26 are connected. The display 24 is composed of a liquid crystal panel capable of displaying images. The operation unit 26 accepts an operation input by a user to the analysis device 100. The operation unit 26 is typically composed of a touch panel, a keyboard, a mouse, and the like.

The controller 22 has, as its main components, a processor 30, a memory 32, a communication interface (I/F) 34, and an input/output I/F 36. These units are connected to each other via a bus to be able to communicate with each other.

The processor 30 is typically an arithmetic processing unit, such as, e.g., a CPU (Central Processing Unit) and a MPU (Micro Processing Unit). The processor 30 controls the operation of each unit of the analysis device 100 by reading and executing the programs stored in the memory 32. Specifically, the processor 30 executes the programs to detect the characteristic X-rays generated from the sample and analyze the detected characteristic X-ray data. In the example of FIG. 1, a single processor is illustrated, but the controller 22 may have a plurality of processors.

The memory 32 is realized by a non-volatile memory, such as, e.g., a RAM (Random Access Memory), a ROM (Read Only Memory), and a flash memory. The memory 32 stores programs to be performed by the processor 30 or data to be used by the processor 30.

The input/output I/F 36 is an interface for exchanging various types of data between the processor 30, the display 24 and the operation unit 26.

The communication I/F 34 is a communication interface for exchanging various types of data with the device body 10, and is implemented by adapters, connectors, and the like. The communication method may be a wireless communication method, such as, e.g., a wireless LAN (Local Area Network), and a wired communication method using a USB (Universal Serial Bus).

Figure 2:
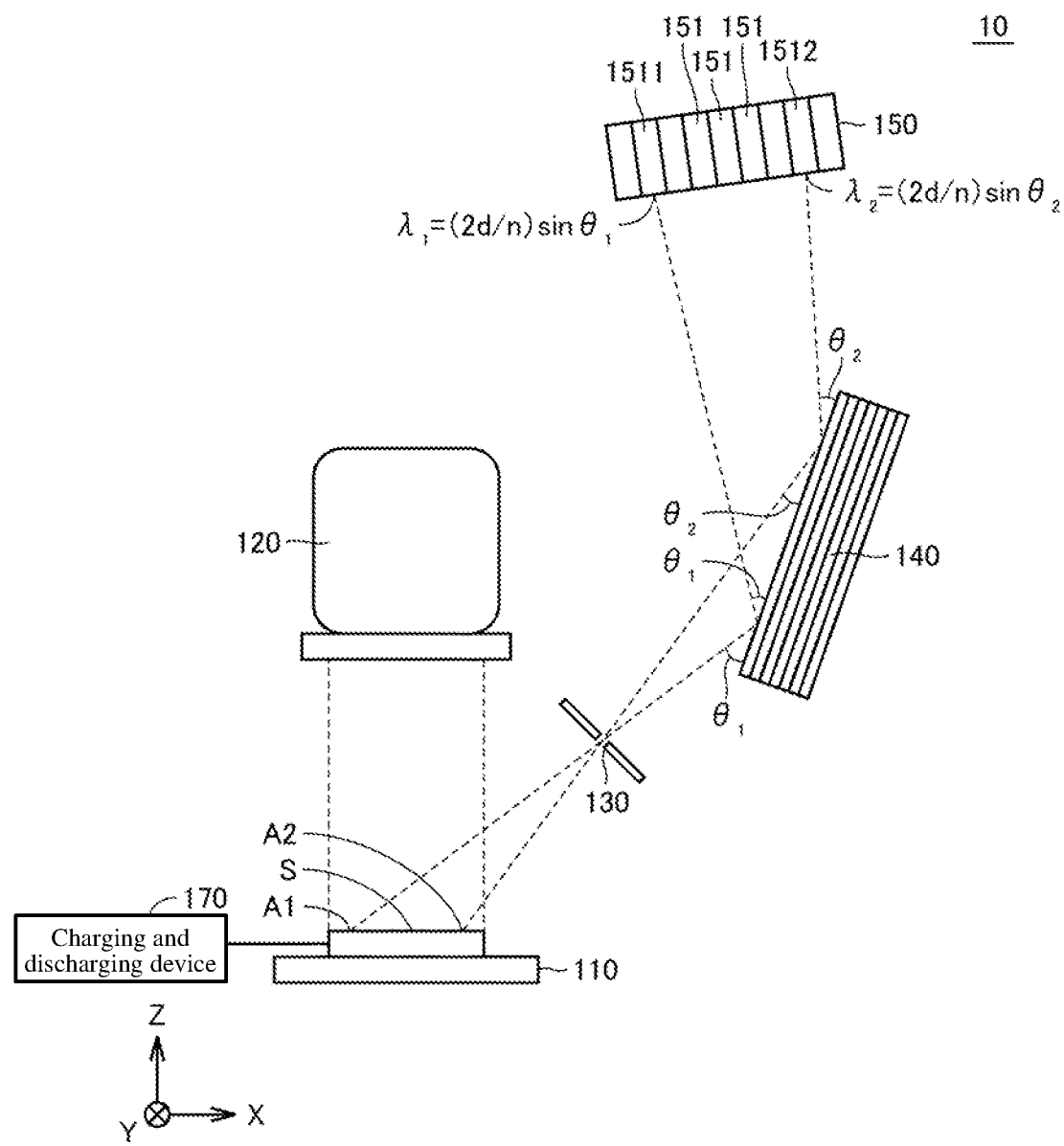
FIG. 2 is a diagram schematically showing an inner configuration of a device body.
Figure 3:
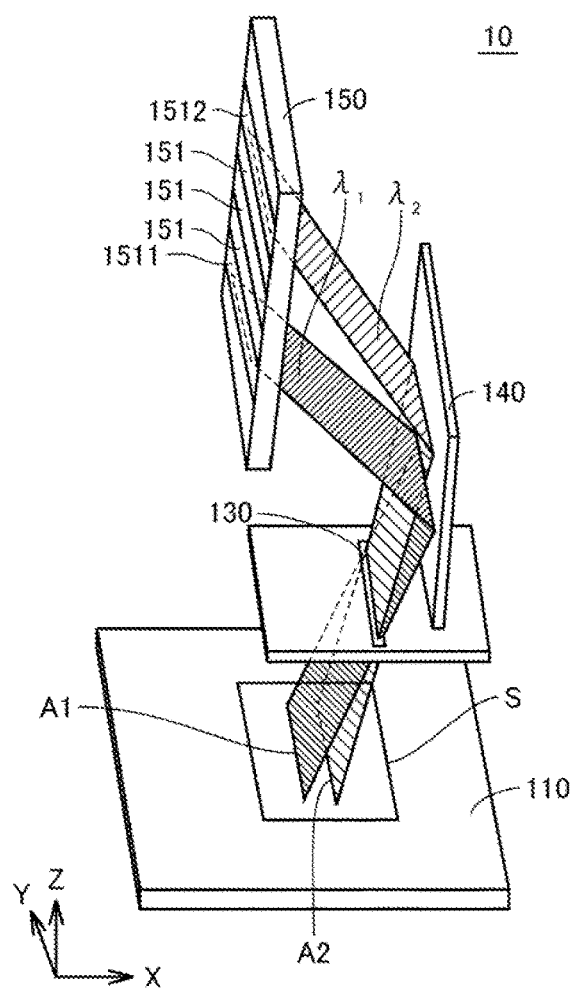
FIG. 3 is a diagram schematically showing an inner configuration of a device body.

FIG. 2 and FIG. 3 are diagrams schematically showing the inner structure of the device body 10. With reference to FIG. 2 and FIG. 3, the device body 10 is provided with a sample holder 110 that holds a sample S, an excitation source 120, a slit 130, a dispersive crystal 140, and a detector 150. In FIG. 2, the surface of the sample holder 110 on which the sample S is held is defined as the X-Y plane, and the direction in which the excitation ray is emitted from the excitation source 120 is defined as the Z-axis direction. Note that the dispersive crystal 140 and the detector 150 constitute the "spectrometer". The sample S may be any of a solid, a liquid, and a gas, and the sample holder 110 corresponding to the state of the sample S is used.

The excitation source 120 is an X-ray source for emitting X-rays as excitation light (excitation ray) to the sample S. An electron-beam source may be used instead of the X-ray source. The excitation light emitted from the excitation source 120 is irradiated onto the surface of the sample S. In the example of FIG. 2, it is configured to emit the excitation light perpendicular to the surface of the sample S, but it may be configured to emit the excitation light at an angle inclined with respect to the surface of the sample S.

In the dispersive crystal 140, a particular crystal plane is parallel to the surface of the dispersive crystal 140. Only certain crystal planes can be used to detect the characteristic X-rays, and characteristic X-rays Bragg-reflected at other crystal planes can be prevented from being erroneously detected.

As shown in FIG. 3, the detector 150 is composed of a plurality of detection elements 151. Each of the plurality of detection elements 151 extends in the Y-axis direction.

Next, the operation of the analysis device 100 according to this embodiment will be described. As shown in FIG. 2, in a state in which the sample S is held by the sample holder 110, when excitation ray is emitted from the excitation source 120 onto the sample S, characteristic X-rays are emitted from the sample S. The characteristic X-rays to be emitted have wavelengths different from each other depending on the material constituting the sample S. In FIG. 2, the characteristic X-rays emitted by the irradiation of the excitation ray emitted from the excitation source 120 to the region from the position A1 to the position A2 pass through the slit 130 and reach the dispersive crystal 140. In FIG. 2, the characteristic X-rays generated at the position A1 and the position A2 are exemplarily indicated by broken lines. The position A2 is a position that is in the positive direction of the position A1 in the X-axis direction. The position A1 and the position A2 extend in the Y-axis direction (see FIG. 3).

The characteristic X-rays emitted from the sample S pass through the slit 130 and reach the dispersive crystal 140. When the angle between the dispersive crystal 140 and the incident characteristic X-rays is θ, the incident angle of the characteristic X-rays is (90−θ) degrees. Because of the angular orientation of the surface of sample S fixed to the sample holder 110 and the surface of the dispersive crystal 140, the characteristic X-rays emitted at the position A1 is incident on the dispersive crystal 140 at the incident angle $(90−θ_1)$ degrees, and the characteristic X-rays emitted at the position A2 are incident on the dispersive crystal 140 at the incident angle $(90−θ_2)$ degrees. In other words, the incident angle of the characteristic X-rays to the dispersive crystal 140 differs depending on the generation position of the characteristic X-rays in the sample S.

Of the characteristic X-rays incident at the incident angle (90−θ) degrees from the sample S, only the characteristic X-rays having a wavelength satisfying λ=(2d/n)sin θ (λ is a wavelength of the characteristic X-rays, d is a crystal plane interval of the dispersive crystal 140, n is the order), which is a Bragg reflection condition, are diffracted by the dispersive crystal 140 and reach the detector 150.

Since the characteristic X-rays diffracted by the dispersive crystal 140 are emitted at the same angle as the incident angle, the Bragg reflected characteristic X-rays are detected by the detection element 151 located at a position of the plurality of detection elements 151 corresponding to the outgoing angle. Specifically, in the case of FIG. 2, of the characteristic X-rays emitted from the position A1, the characteristic X-rays satisfying the wavelength λ1=(2d/n)sin $θ_1$ are detected by the detection element 1511. Also, of the characteristic X-rays emitted from the position A2, the characteristic X-rays satisfying the wavelength λ2=(2d/n)sin $θ_2$ are detected by the detection element 1512.

Thus, for each of the plurality of detection elements, the characteristic X-rays of a wavelength satisfying the Bragg condition of different diffracted angles are detected. In other words, it is possible to recognize the wavelength contained in the characteristic X-rays by knowing the detection element at which the characteristic X-ray is detected. On the other hand, the wavelength of the characteristic X-rays varies from substance to substance. Thus, by identifying the detection element in which the characteristic X-rays were detected by the detector 150, the materials contained in the sample of the analysis target can be identified.

As described above, the spectrometer of the device body 10 detects the intensity for each wavelength by dispersing the characteristic X-rays generated by the sample S irradiated with the excitation ray. The device body 10 transmits the intensity (intensity per detection element) for each detection element to the signal processing device 20. With this, the signal processing device 20 can acquire a plurality of wavelengths and the intensities of the characteristic X-rays corresponding to the respective plurality of wavelengths.

Next, the calculation of the peak energy by the signal processing device 20 will be described. For the energy E and the wavelength λ, the formula E=hc/λ holds. Here, h is the Planck constant, and c is the speed of light. With this formula, the signal processing device 20 obtains the energy and the intensity of the characteristic X-rays corresponding to the energy. The signal processing device 20 measures the energy at which the intensity of the characteristic X-ray peaks (hereinafter referred to as "peak energy").

Further, the analysis device 100 according to this embodiment can adjust the mean energy resolution by adjusting the size and the arrangement of the dispersive crystal 140 and the size and the arrangement of the detector 150. Note that the mean energy resolution is defined by the value obtained by dividing the difference between the maximum value and the minimum value of the energy of the characteristic X-rays incident on the detector 150 through the slit 130 and the dispersive crystal 140 from the irradiated area of the sample surface by the number of detection elements of the detector 150. The maximum value and the minimum values of the characteristic X-ray energy are determined by the relative positional relation of the sample S, the dispersive crystal 140, and the detector 150, and the size of the detector 150 in the direction perpendicular to the slit 130.

The analysis device 100 according to this embodiment can distinguish between the Kα X-ray and the Kβ X-ray or between the Lα X-ray and the Lβ X-ray for any of the metals by setting the mean energy resolution to 20 eV or less, preferably 2 eV or less, and can calculate the peak energy of the $Kα_1$ X-ray and the peak energy of the $Kα_2$ X-ray. Note that the calculation of the peak energy is realized by any method, such as, e.g., the technique described in Japanese Unexamined Patent Application Publication No. 2017-223638, for example. And, the $Kα_1$ X-ray is based on the transition of electrons from the L3 level ($2p_{3/2}$ track) which is the subshell of the L-shell to the K-shell. The $Kα_1$ X-ray is based on the transition of electrons from the L2 level ($2p_{1/2}$ track) which is the subshell of the L-shell to the K-shell.

In the following description, an elemental metal is referred to as "metal simple substance", and a compound containing the metal is referred to as "metal compound"

An unknown sample S may contain a metal simple substance and a metal compound of this metal and other elements. For example, when a metal simple substance is Fe, the metal compound is $Fe_3O_4$ and $Fe_2O_3$. The user may wish to calculate the mean valence of the metal simple substance and the metal in two or more types of compounds each containing the metal in their compositions, which are contained in an unknown sample. The mean valence is expressed as the sum of the multiplication values obtained by multiplying the valence of each of the metal simple substance and the metal compound by the composition ratio of each material in the unknown sample S. For example, in cases where the composition ratio between Fe (metal simple substance), $Fe_3O_4$, and $Fe_2O_3$ (metal compounds) in an unknown sample is P:Q:R, the valence of Fe is 0, the valence of Fe in $Fe_3O_4$ is 2.6667, and the valence of Fe in $Fe_2O_3$ is 3. Therefore, the mean valence is $(P \times 0 + Q \times 2.6667 + R \times 3)/(P+Q+R)$.

In addition, in a case where a mean valence is calculated by an analysis device, a known sample is used to prepare a calibration curve in advance, and the mean valence of the unknown sample is calculated using the calibration curve. As such a calibration curve, for example, as disclosed in Non-Patent Document 1, there is known one in which a peak energy and a valence of a known sample are associated with each other. Here, in a case where a calibration curve is a complex function, the amount of calculation for generating this calibration curve may sometimes be increased. Therefore, a calibration curve is preferably a simple function, such as, e.g., a linear function.

Non-Patent Document 1 discloses a calibration curve of a linear function acquired from the relation between the peak energy and the valence of two types of compounds (NiO and $LiNiO_2$) containing a certain metal. However, in the method of Non-Patent Document 1, since the relation between the peak energy and the valence for a metal simple substance of valence 0 is remarkably deviated from a calibration curve as described later, the mean valence of the metal cannot be correctly calculated when the sample contains a metal simple substance.

The inventor found that by performing various tests to solve this issue, the peak energy of the $K\alpha_1$ X-ray and the peak energy of the $K\alpha_2$ X-ray move differently with respect to the valence between a metal simple substance and a metal compound. Based on this finding, the inventor has found that by using a parameter using the peak energy of the $K\alpha_1$ X-ray and the peak energy of the $K\alpha_2$ X-ray, the valence of the metal simple substance and the valence of two or more types of compounds including a metal can be expressed by a linear relation (i.e., the calibration curve becomes a linear function). With this, even in cases where a metal simple substance of a valence 0 is contained in a sample, it is possible to suppress the deterioration of the calculation accuracy of the mean valence.

Figure 4:
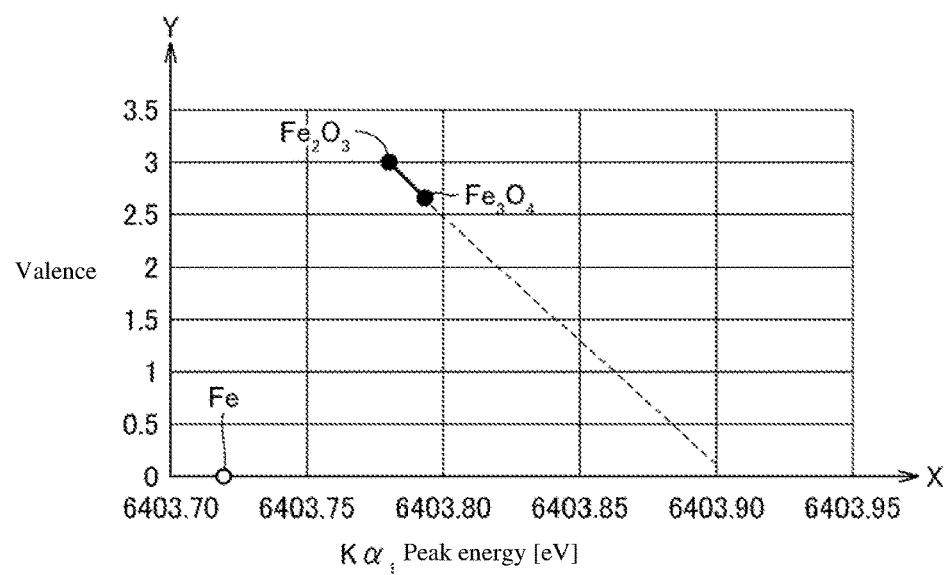
FIG. 4 is a diagram showing the relation between the valence of each of Fe, $Fe_2O_3$, $Fe_3O_4$ and the peak energy of the $K\alpha_1$ X-ray.
Figure 5:
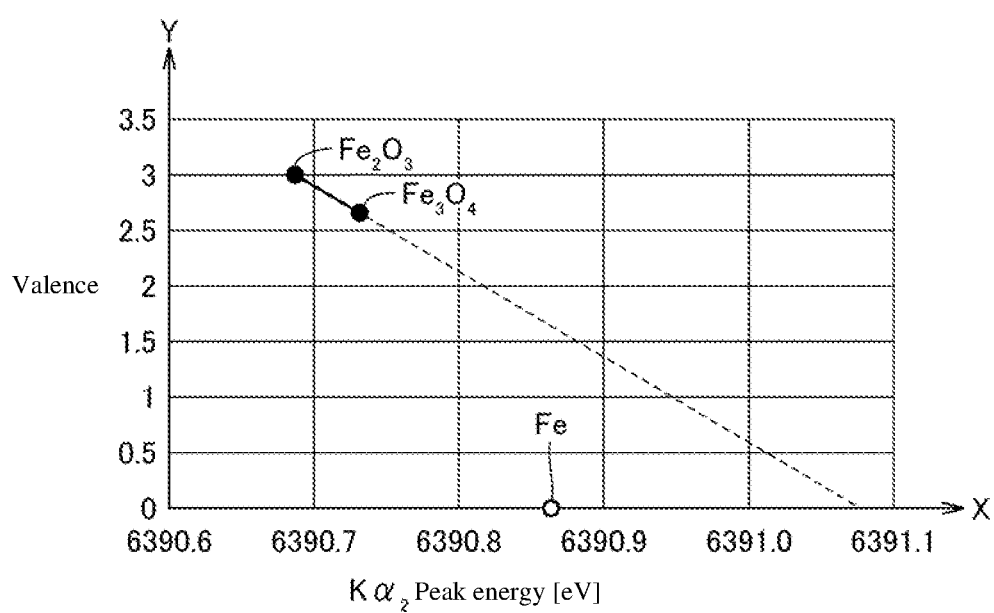
FIG. 5 is a diagram showing the relation between the valence of each of $Fe_2O_3$, $Fe_3O_4$, and Fe and the peak energy of the $K\alpha_2$ X-ray.

FIG. 4 is a diagram showing the relation between the valence of each of $Fe_2O_3$, $Fe_3O_4$, and the peak energy of the $K\alpha_1$ X-ray. FIG. 5 is a diagram showing the relation between the valence of each of $Fe_2O_3$, $Fe_3O_4$, and Fe and the peak energy of the $K\alpha_2$ X-ray. The horizontal axis of FIG. 4 and that of FIG. 5 show the peak energy of the $K\alpha_1$ X-ray and the peak energy of the $K\alpha_2$ X-ray, respectively. The vertical axis of FIG. 4 and FIG. 5 shows the valence. As can be seen from FIG. 4 and FIG. 5, the relations between peak energy and valence for the three metals and the metal compound are not linear. Specifically, the value of the valence to the peak energy for a metal simple substance Fe deviates significantly from a calibration curve calculated based on the case of $Fe_2O_3$ and $Fe_3O_4$.

In FIG. 4, the plot of $Fe_2O_3$ and the plot of $Fe_3O_4$ are linearly related. However, there is no plot of Fe on the straight line connecting these plots. Therefore, the straight line connecting these plots is not preferable as a calibration curve. FIG. 5 is a diagram showing the relation between the valence of each of $Fe_2O_3$, $Fe_3O_4$, and Fe and the peak energy of the $K\alpha_2$ X-ray. Also in FIG. 5, there is no plot of Fe on the straight line connecting the plot of $Fe_2O_3$ and the plot of $Fe_3O_4$ to generate a calibration curve of a primary function. Therefore, the straight line connecting these plots is also not preferable as a calibration curve. In FIG. 4 and FIG. 5, it is conceivable that a curve connecting the plot of $Fe_2O_3$, the plot of $Fe_3O_4$, and Fe is used as a calibration curve, but such a calibration curve results in a complex function. Therefore, the amount of calculation for generating the calibration curve increases.

In view of the results of FIG. 4 and FIG. 5, the inventor has found that the relation between the parameter in which "the peak energy of the $K\alpha_1$ X-ray" and "the peak energy of the $K\alpha_2$ X-ray" are combined and the valence becomes linear. Specifically, the inventor has found that the valences of a metal Fe, $Fe_2O_3$, and $Fe_3O_4$ become linearly related by using $(K\alpha_1 - n \cdot K\alpha_2)$ which is a parameter obtained by subtracting the value obtained by multiplying the peak energy of the $K\alpha_2$ X-ray of the metal by a coefficient n from the peak energy of the $K\alpha_1$ X-ray of the metal (Fe in this embodiment) as a new index (see FIG. 9 to FIG. 12 below). In this embodiment, in order to simplify the calculation process of the mean valence, it is defined that the calibration curve is a linear function $y = px + q$ (hereinafter also referred to as formula (1)). Here, x is the above-described parameter $(K\alpha_1 - n \cdot K\alpha_2)$, and y is a mean valence.

Hereinafter, the peak energy of the $K\alpha_1$ X-ray of a metal simple substance (e.g., Fe) is denoted as a peak energy m1. The peak energy of the $K\alpha_2$ X-ray of this metal simple substance is denoted as a peak energy m2. The valence of a metal first metal compound (e.g., $Fe_3O_4$) which is one of metal compounds of two types of metal compounds is denoted as a valence v. The peak energy of the $K\alpha_1$ X-ray of this metal compound is denoted as a1. The peak energy of the $K\alpha_2$ X-ray of this metal compound is denoted as a2. Further, the valence of a second metal compound (e.g., $Fe_2O_3$) which is the other metal compound of the two types of metal compounds is denoted as a valence w. The peak energy of the $K\alpha_1$ X-ray of this metal compound is denoted as b1. The peak energy of the $K\alpha_2$ X-ray of this metal compound is denoted as b2. FIG. 6 is a table summarizing these values. These two metal compounds include a metal (Fe) and differ from each other in the valence of the metal.

Note that the valence of a metal simple substance, the valence v contained in the first metal compound, and the valence w contained in the second metal compound are substance-specific values. The valence of a metal simple substance is "0". In a case where a first metal compound is $Fe_3O_4$, the valence v is 2.6667. In a case where a second metal compound is $Fe_2O_3$, the valence w is 3.0000.

As described above, the analysis device 100 can calculate the peak energies m1, m2, a1, a2, b1, and b2. Also, for each of the valence of the first metal compound and the valence of the second metal compound, the analysis device 100 accepts inputs by the user.

By substituting the valence of the metal of FIG. 6 into y in the above-described formula (1) and substituting the "$m1 - n \cdot m2$" of the metal into x, the following formula (2) is produced.

$$0 = p \cdot (m1 - n \cdot m2) + q \qquad (2)$$

Similarly, by substituting the valence v of the first metal compound into y of the above-described formula (1) and substituting the "$a1 - n \cdot a2$" of the first metal compound into x, the following formula (3) is generated.

$$v = p \cdot (a1 - n \cdot a2) + q \qquad (3)$$

Similarly, by substituting the valence w of the second metal compound (e.g., $Fe_2O_3$) to y of the above-described formula (1) and substituting "$b1 - n \cdot b2$" of the second metal compound to x, the following formula (4) is generated.

$$w = p \cdot (b1 - n \cdot b2) + q \qquad (4)$$

As shown in the formulas (2) to (4), simultaneous linear formulas with three variables of a coefficients n, a slope p, and an intercept q are generated. By solving the simultaneous linear formulas, the coefficient n, the slope p, and the intercept q are expressed by the following formulas (5) to (7).

$$n=\{(v-w)\cdot m1-v\cdot b1+w\cdot a1\}/\{(v-w)\cdot m2-v\cdot b2+w\cdot a2\} \quad (5)$$

$$p=(v-w)/\{(a1-b1)-n\cdot(a2-b2)\} \quad (6)$$

$$q=\{w\cdot(a1-n\cdot a2)-v\cdot(b1-n\cdot b2)\}/\{(a1-a2)-n\cdot(a2-b2)\} \quad (7)$$

By the slope p and the intercept q calculated by the formulas (5) to (7), the y=px+q, which is calibration curve, is generated, and the coefficient n is obtained.

By using the calibration curve generated as described above, the analysis device 100 can calculate a mean valence with high accuracy even in cases where a metal simple substance is contained in a sample because in the case of a metal simple substance and in the case of a compound, it becomes a linear relation.

Figure 7:
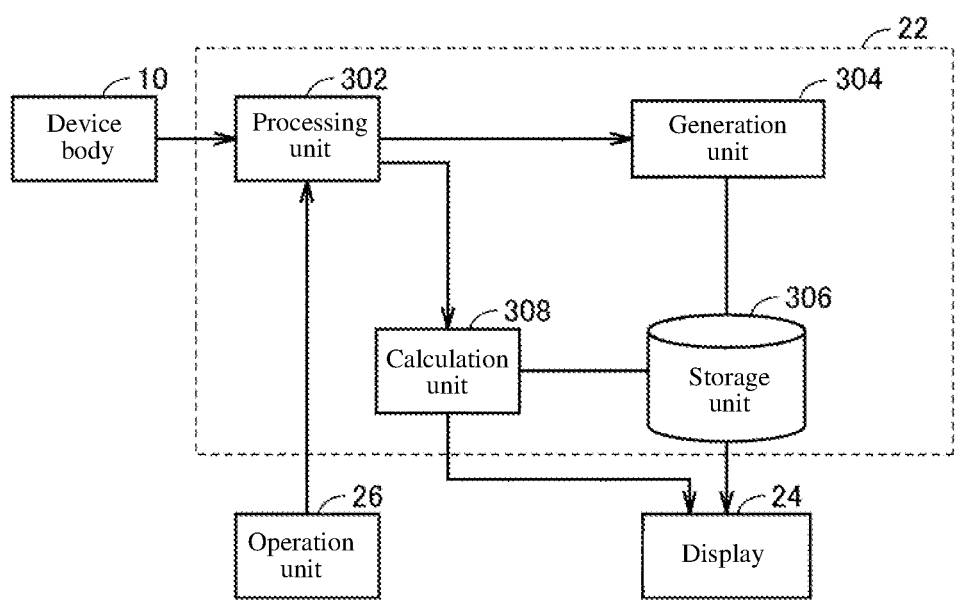
FIG. 7 is a functional diagram of a controller.

Next, the flow of the generation of the calibration curve by the controller 22 will be described. The calibration curve may be generated after the production of the analysis device 100 and before the shipment of the analysis device 100, or may be generated by a user's manipulation after the shipment of the analysis device 100. FIG. 7 is a functional block diagram of a controller 22 of the signal processing device 20. The controller 22 is provided with a processing unit 302, a generation unit 304, a storage unit 306, and a calculation unit 308.

The processing unit 302 acquires the valences v and w of each of the first metal compound and the second metal compound input by the operation of the operation unit 26 by the user. Note that the valence of each of the first metal compound and the second metal compound may be stored in advance in the storage unit 306 or the like.

The person who generates the calibration curve (e.g., the manufacturer of the analysis device 100) places a metal simple substance (known sample) on the sample holder 110 and causes the device body 10 to emit excitation ray to the metal simple substance. With this, the processing unit 302 acquires the peak energy m1 of the $K\alpha_1$ X-ray of the metal simple substance and the peak energy m2 of the $K\alpha_2$ X-ray of the metal simple substance. The manufacturer places the first metal compound (known sample) on the sample holder 110 and makes the device body 10 emit excitation ray to the first metal compound. Thus, the processing unit 302 acquires the peak energy a1 of the $K\alpha_1$ X-ray of the first metal compound and the peak energy a2 of the $K\alpha_2$ X-ray of the first metal compound. The manufacturer places the second metal compound (known sample) on the sample holder 110 and makes the device body 10 emit excitation ray to the second metal compound. With this, the processing unit 302 acquires the peak energy m1 of the $K\alpha_1$ X-ray of the second metal compound and the peak energy m2 of the $K\alpha_2$ X-ray of the second metal compound. Note that each of the metal simple substance, the first metal compound, and the second metal compound is formed into powder by being pressure-molded and placed on the sample holder 110.

The acquired valences v and w and the peak energies m1, m2, a1, a2, b1, and b2 are output to the generation unit 304. The generation unit 304 calculates the parameter of the calibration curve (slope p, intercept q) and the coefficient n. Specifically, the generation unit 304 calculates the parameter and the coefficient n of the calibration curve by substituting the valences v and w and the peak energies m1, m2, a1, a2, b1, and b2 into the formulas (5) to (7). The calculated parameter and the coefficient n of the calibration curve are stored in the storage unit 306.

Figure 9:
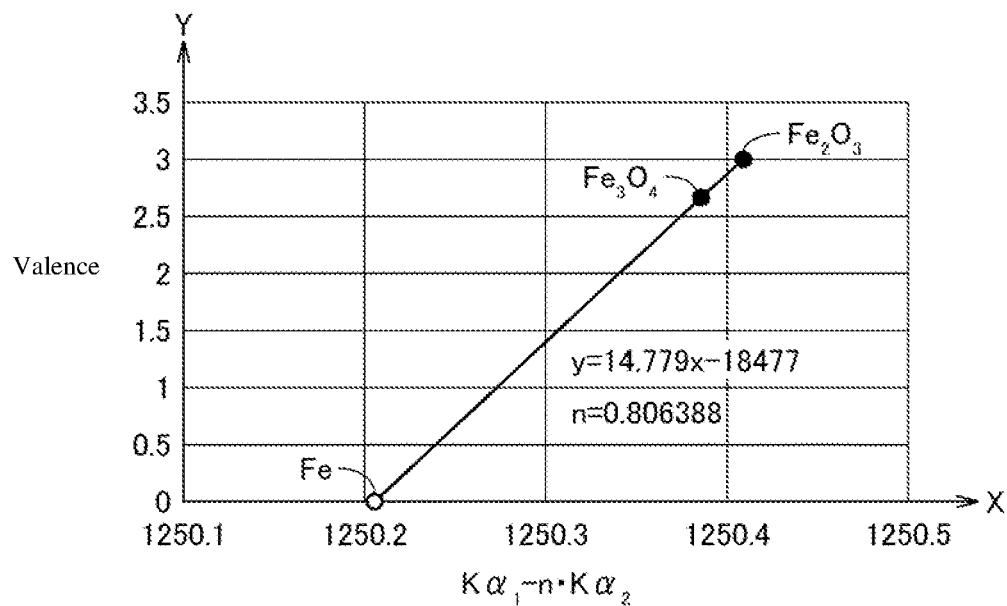
FIG. 9 is a diagram showing an example of a calibration curve for a metal Fe.

FIG. 8 is a diagram showing a specific example of each value of the metal Fe, the first metal compound $Fe_2O_3$ and the second metal compound $Fe_3O_4$. In the example of FIG. 9, the valence v=2.6667 and the valence w=3.0000. The peak energy m1=6403.719, the peak energy a1=6403.793, and the peak energy b1=6403.780. the peak energy m2=6390.864, the peak energy a2=6390.731, and the peak energy b2=6390.687.

By substituting the valences v and w and the peak energies m1, m2, a1, a2, b1, and b2 into the formulas (5) to (7), n=0.806388, p=14.779, and q=−18477 are calculated in the generation unit 304. FIG. 9 is a diagram showing a calibration curve generated using the calculated slope p, intercept q, and coefficient n. In FIG. 9, the vertical axis (Y-axis) represents the valence, and the horizontal axis (X-axis) represents $K\alpha_1-n\cdot K\alpha_2$. This calibration curve is y=14.779x−18477 and n=0.806388. In the examples of FIG. 4 and FIG. 5, the valences of $Fe_2O_3$, and $Fe_3O_4$ and the metal Fe were not linearly related. On the other hand, as shown in FIG. 9, in the calibration curve generated by the generation unit 304 of this embodiment, the valences of $Fe_2O_3$ and $Fe_3O_4$ and the metal Fe are linearly related. Therefore, by using the calibration curve of FIG. 9, the analysis device 100 can accurately calculate a mean valence of a metal Fe in a sample even in cases where a metal simple substance is contained in a sample.

Figure 10:
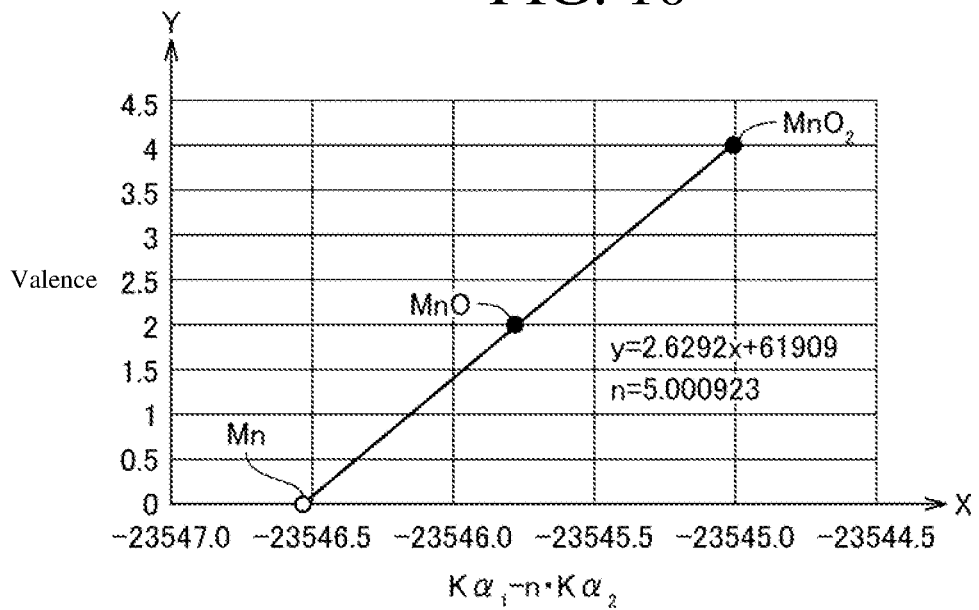
FIG. 10 is a diagram showing an example of a calibration curve for a metal Mn.
Figure 11:
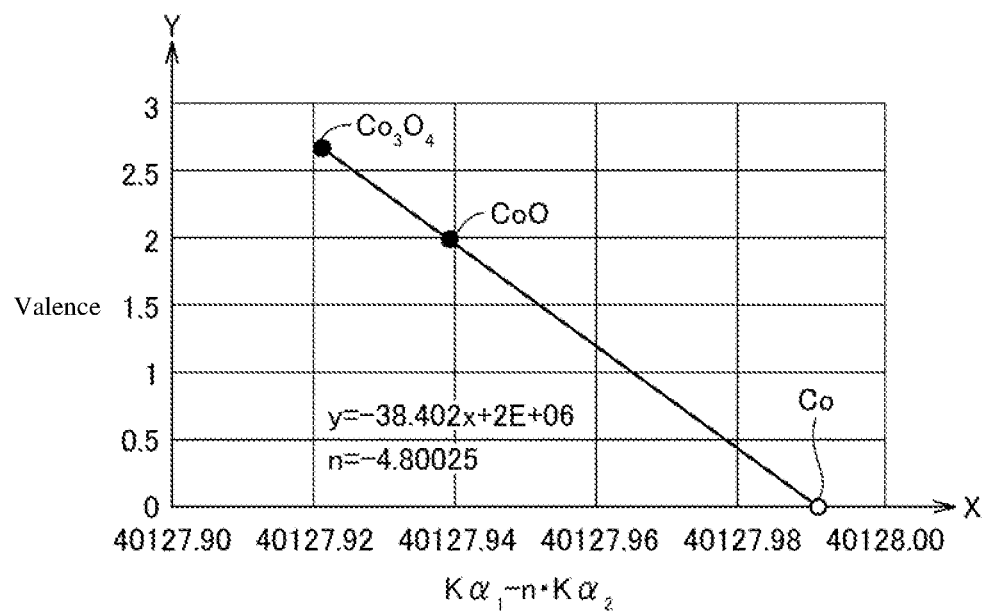
FIG. 11 is a diagram showing an example of a calibration curve for a metal Co.
Figure 12:
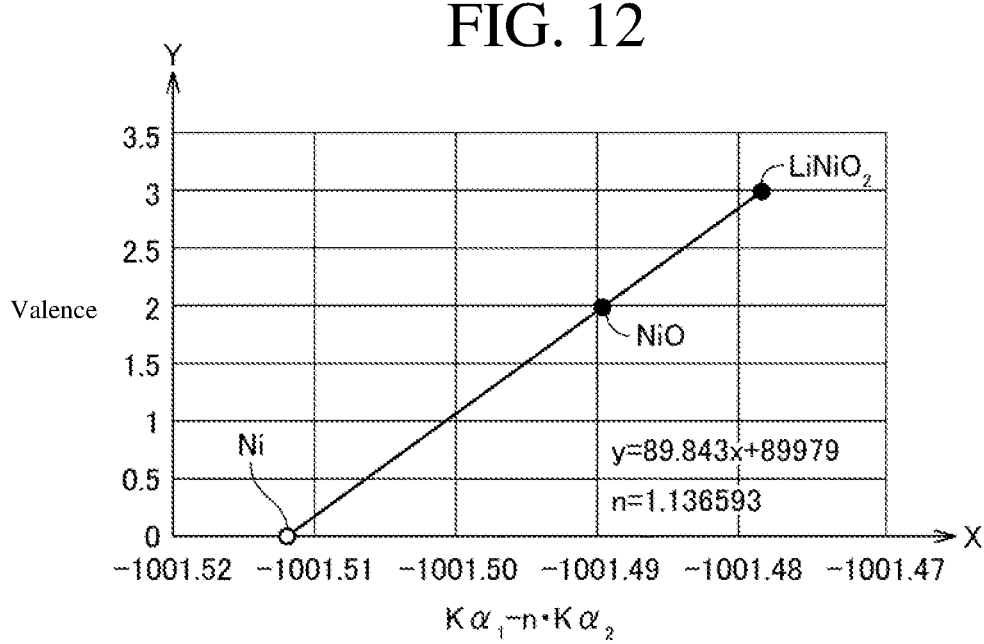
FIG. 12 is a diagram showing an example of a calibration curve for a metal Ni.

FIG. 10 is an example of a calibration curve generated by the generation unit 304 in a case of a metal Mn, a first compound MnO, and a second compound $MnO_2$. FIG. 11 is an example of a calibration curve generated by the generation unit 304 in a case of a metal Co, a first compound CoO, and a second compound $CO_3O_4$. FIG. 12 is an example of a calibration curve generated by the generation unit 304 in a case of a metal Ni, a first compound NiO, and a second compound $LiNiO_2$. The storage unit 306 can store, for example, at least one calibration curve of the calibration curves shown in FIG. 9 to FIG. 12.

Next, a method for calculating a mean valence of a metal of an unknown sample (analysis target sample) will be described. FIG. 13 is an example of a flowchart showing a method of calculating a mean valence. The user recognizes that at least one of a metal simple substance, a first metal compound, and a second metal compound is contained in an unknown sample. However, the user does not recognize the mean valence of the metal contained in the unknown sample, and the purpose of the analysis device 100 is to calculate this mean valence.

The storage unit 306 stores a plurality of calibration curves for each of the metals whose mean valence is to be measured. For example, the metal Fe is associated with the calibration curve described in FIG. 9, the metal Mn is associated with the calibration curve described in FIG. 10, the metal Co is associated with the calibration curve described in FIG. 11, and the metal Ni is associated with the calibration curve described in FIG. 12. The user inputs a metal whose mean valence is to be calculated using the operation unit 26 into the signal processing device 20. The signal processing device 20 determines the calibration curve corresponding to the input metal. Here, the unknown sample includes at least one of Fe, $Fe_2O_3$, and $Fe_3O_4$, and the user inputs the metal Fe as the metal whose mean valence is to be calculated. The signal processing device 20 calls the calibration curve (i.e., the calibration curve in FIG. 9) corresponding to the metal Fe from the storage unit 306.

In Step S2, based on the detection signal from the device body 10, the processing unit 302 acquires the peak energy of the $K\alpha_1$ X-ray of the metal Fe and the peak energy of the $K\alpha_2$ X-ray of the metal Fe contained in the unknown sample. The acquisition of the peak energy of the $K\alpha_1$ X-ray of the metal Fe and the peak energy of the $K\alpha_2$ X-ray of the metal Fe are performed based on the intensity per wavelength of characteristic X-rays detected by the device body 10. The acquired peak energy $K\alpha_1$ and the peak energy $K\alpha_2$ are output to the calculation unit 308.

Next, in Step S4, the calculation unit 308 calculates the mean valence of the metal Fe contained in the sample by applying the peak energy $K\alpha_1$ and the peak energy $K\alpha_2$ of the metal Fe to the called calibration curve. Specifically, the calculation unit 308 substitutes the peak energy $K\alpha_1$ and the peak energy $K\alpha_2$ of the metal Fe into "$K\alpha_1 - n \cdot K\alpha_2$", substitutes the substituted values into x of y=14.799x−18477, which is the calibration curve of FIG. 9, and calculates the mean valence. The calculation unit 308 displays the calculated mean valence on the display 24 to notify the user. Note that the mean valence may be output, for example, by printing a mean valence on a sheet of paper. The processing unit 302 and the calculation unit 308 correspond to the "operation unit" of the present disclosure.

As described above, the analysis device 100 generates a calibration curve in which the valences of the metal simple substance and two types of metal compounds is linear based on the peak energy of the $K\alpha_1$ line and the peak energy of the $K\alpha_2$ X-ray of the metal simple substance, the peak energy of the $K\alpha_1$ X-ray and the peak energy of the $K\alpha_2$ X-ray of each of the two types compounds of the metal, and the valence of the metal in each of the two types of metal compounds. The analysis device 100 then calculates the mean valence of the target metal contained in the unknown sample by applying the curve peak energy of the $K\alpha_1$ X-ray for the target metal and the peak energy of the $K\alpha_2$ X-ray for the metal, detected for the unknown sample to the calibration curve. As described above, in the calibration curve of this embodiment, since it is also considered the case in which the metal simple substance is contained in the unknown sample, a mean valence of a target metal can be accurately calculated even in a case where a metal simple substance is contained in an unknown sample.

Further, in this embodiment, the calibration curve is expressed as a linear function of y=px+q. Therefore, compared with an analysis device which generates a calibration curve, which is a complex function, a calibration curve can be generated with a smaller amount of operation.

Further, in this embodiment, the coefficient n, the slope p, and the intercept q are obtained by the above-described formulas (5) to (7). Therefore, the analysis device 100 can generate a calibration curve by a relatively simple operation.

Further, the analysis device 100 of this embodiment displays a calibration curve on the display 24. Therefore, the user can grasp the used calibration curve by the displayed calibration curve used for the calculation of the mean valence.

In the above-described description, the description has been made in which the calibration curve used for the analysis of the unknown sample which can be composited with a metal simple substance and two types of metal compounds and the calibration curve used for the analysis are generated. Next, a description will be directed to a case in which an unknown sample that can be composed of a metal simple substance and three or more metal compounds is analyzed and a case in which the calibration curve used for the analysis is generated. One example of the unknown sample of this embodiment is an electrode active material contained in a secondary battery. The electrode active material may be a positive electrode active material or a negative electrode active material.

As an example in which the valence of the target metal contained in the unknown sample changes in four stages, the charge/discharge operation in a secondary battery can be exemplified. There is a case in which the quality of the secondary battery is inspected by causing a conversion reaction of an electrode active material contained in a secondary battery by repeating charging and discharging of the secondary battery. For example, the conversion reaction of an iron fluoride-based secondary battery containing a metal Fe and a fluoride (metal compound) of Fe is represented by the following formulas (a) to (c). The charging and discharging of the secondary battery is performed, for example, by the charging and discharging device 170.

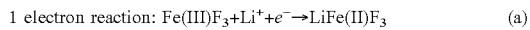

1 electron reaction: $Fe(III)F_3 + Li^+ + e^- \rightarrow LiFe(II)F_3$     (a)

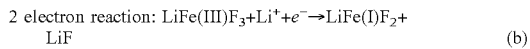

2 electron reaction: $LiFe(III)F_3 + Li^+ + e^- \rightarrow LiFe(I)F_2 + LiF$     (b)

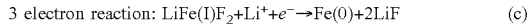

3 electron reaction: $LiFe(I)F_2 + Li^+ + e^- \rightarrow Fe(0) + 2LiF$     (c)

Generally, it is better to change a mean valence of a specified metal (here, Fe) greatly by performing charging and discharging of a secondary battery. For example, the secondary battery is evaluated as "Pass" when the amount of change in the mean valence of Fe by discharging the fully discharged secondary battery for a predetermined time is larger than a predetermined value, and the amount of change in the mean valence of Fe by fully charging the sufficiently discharged secondary battery is larger than a predetermined value. On the other hand, a secondary battery is evaluated as "Fail" when the amount of change in the mean valence of Fe by discharging the fully charged secondary battery for a predetermined period is smaller than a predetermined value. Further, the secondary battery is also evaluated as "Fail" when the amount of change in the mean valence of Fe by charging for a predetermined period with respect to a secondary battery which is sufficiently discharged is smaller than a predetermined value is also rejected.

In a case in which conversion reactions shown in formulas (a) to (c) have been performed, Fe, $FeF_3$, $LiFeF_3$, and $LiFeF_3$ are contained in the unknown sample (iron fluoride secondary battery). Thus, the unknown sample contains a metal simple substance (Fe) and three metal compounds ($FeF_3$, $LiFeF_3$, $LiFeF_2$). Hereinafter, in some cases, $LiFeF_2$ is referred to as a first metal compound, $LiFeF_3$ is referred to as a second metal compound, and $FeF_3$ is referred to as a third metal compound.

Next, the generation of a calibration curve for the analysis of an unknown sample that can be composited of three types of metal compounds is described. The analysis device 100 acquires the peak energy of the $K\alpha_1$ X-ray and the peak energy of the $K\alpha_2$ X-ray for each of a metal simple substance and three metals compounds, which are a known sample.

Specifically, a metal simple substance is formed into powder by being pressure-molded and placed on a sample holder 110. Then, X-rays are emitted to the metal simple substance, so that the processing unit 302 acquires the peak energy m1 of the $K\alpha_1$ X-ray of the metal and the peak energy m2 of the $K\alpha_2$ X-ray of the metal. Further, the first metal compound is formed into powder by being pressure-molded and placed on the sample holder 110. The processing unit 302 acquires the peak energy a1 of the $K\alpha_1$ X-ray of the first metal compound and the peak energy a2 of the $K\alpha_2$ X-ray of the first metal compound. Further, the second metal compound is formed into powder by being pressure-molded and placed in sample holder 110. The processing unit 302 acquires peak energy b1 of the $K\alpha_1$ X-ray of the second metal compound and the peak energy b2 of the $K\alpha_2$ X-ray of the second metal compound. Further, the third metal compound is formed into powder by being pressure-molded and placed on the sample holder 110. The processing unit 302 acquires the peak energy c1 of the $K\alpha_1$ X-ray of the third metal compound and the peak energy c2 of the $K\alpha_2$ X-ray of the third metal compound.

The valence v of the metal (Fe) for the first metal compound, the valence w of the metal (Fe) for the second metal compound, and the valence s of the metal (Fe) for the third metal compound are input by the user, respectively. The processing unit 302 acquires the valence v, the valence w, and the valence s. The three or more types of metal compounds differ from each other in the valence of the metal (Fe).

The acquired valences v, w, and s and the peak energies m1, m2, a1, a2, b1, b2, c1, and c2 are output by the generation unit 304. The generation unit 304 calculates the coefficient n, the slope p, and the intercept q by applying the least-squares method to each of the valences v, w, and s and the peak energies m1, m2, a1, a2, b1, b2, c1, and c2.

FIG. 14 is a diagram showing an image in which a calibration curve (slope p and intercept q) and the coefficient n are calculated by the least-squares method. In the example of FIG. 14, each of the metal, the first metal compound, the second metal compound, and the third metal compound is plotted. The generation unit 304 calculates the calibration curve (slope p, intercept q) and the coefficient n such that the error from each of the plots of the metal, the first metal compound, the second metal compound, and the third metal compound is minimal.

Next, an example of an iron oxide-based secondary battery different from an iron fluoride-based secondary battery will be described. An iron-fluoride-based secondary battery contains a metal Fe and a Fe oxide (metal compound). The conversion reactions of the iron-oxide-based the secondary battery are shown by the following formulas (d) to (f). Also in this case, the valence of Fe changes in four steps.

1 electron reaction: $Fe(III)_2O_3 + 2Li^+ + 2e^- \rightarrow Li_2Fe(II)_2O_3$ (d)

2 electron reaction: $Li_2Fe(II)_2O_3 + 2Li^+ + 2e^- \rightarrow 2LiFe(I)O + Li_2O$ (b)

3 electron reaction: $2LiFe(I)O + 2Li^+ + 2e^- \rightarrow 2Fe(0) + 2Li_2O$ (c)

In a case where the conversion reactions shown in formulae (d) to (f) are performed, an unknown sample (ion-oxide-based secondary battery) contains Fe, $Fe_2O_3$, $Li_2Fe_2O_3$, and LiFeO. That is, an unknown sample contains one metal simple substance (Fe) and three metal compounds ($Fe_2O_3$, $Li_2Fe_2O_3$, and LiFeO). The generation unit 304 can generate a calibration curve for the iron oxide-based secondary battery using a method similar to that described for the iron fluoride-based secondary battery.

In addition, in cases where an unknown sample contains a metal simple substance and four or more metal compounds, the generation unit 304 calculates the coefficient n, the slope p, and the intercept q by the least-squares method so that the error from the plot of the one metal simple substance and the plot of each of the 4 or more metal compounds is minimized.

As described above, the signal processing device 20 generates a calibration curve based on: the peak energy of the $K\alpha_1$ X-ray, the peak energy of the $K\alpha_2$ X-ray of a metal simple substance; the peak energy of the $K\alpha_1$ X-ray and the peak energy of the $K\alpha_2$ X-ray of the metal of each of the three or more types of compounds; and the valence of the metal contained in each of the three or more types of compounds. Thus, the signal processing device 20 can generate a calibration curve that reflects the parameter of each of the metal simple substance and the three or more types of compounds.

Next, an example of calculating a composition ratio of an unknown sample will be described. There is a case in which a user knows that an unknown sample is composed of a first substance and a second substance whose valence in the metal is different from each other. Each of the first substance and the second substance is a metal simple substance or a metal compound. Each of the first substance and the second substance whose valence of the metal is different from each other is, for example, $Fe_3O_4$ and $Fe_2O_3$.

In this case, the calculation unit 308 may calculate the composition ratio of the unknown sample based on the calculated mean valence ym and output the composition ratio. Hereinafter, the valence of the first substance is referred to as "valence i (I=1, 2, ..., 7)" and the valence of the second substance is referred to as "valence j (j=1, 2, ..., 7)". In this case, the ratio of the first substance to the second substance is represented by the following formula (8).

$$\text{First substance:Second substance} = 1:(ym-i)/(j-ym) \quad (8)$$

where $i < ym < j$.

FIG. 15 shows a diagram in a tabular form showing all possible composition ratios of the first substance and the second substance when the mean valence ym=2.5. In FIG. 15, the vertical direction of the paper surface represents i, and the horizontal direction of the paper surface represents j. In the example of FIG. 15, fifteen combinations are displayed.

In FIG. 15, for example, in a case where the valence i of the first substance is 1 and the valence j of the second substance is 5, the corresponding value is 0.6. Therefore, the first substance:the second substance=1:0.6=5:3.

The calculation unit 308 displays all possible composition ratios of the first substance and the second substance on the display 24 by the tables shown in FIG. 15.

When the analysis device 100 outputs all composition ratios in which the first substance and the second substance can take, the user can recognize all composition ratios. In addition, the analysis device 100 can calculate a composition ratio between the first substance and the second substance based on the above-described formula (8).

There is a case in which the user can grasp the valence of the first substance and the valence of the second substance, but cannot grasp the composition ratio of the first substance to the second substance by other analytical techniques, such as, e.g., the X-ray diffraction. In this case, by comparing the valence of the first substance and the valence of the second substance input by the user with all the possible composition ratios of the first substance and the second substance, the calculation unit 308 determines the corresponding composition ratio of the valence of the first substance to the valence of the second substance and displays the determined composition ratio on the display 24

FIG. 16 is a diagram showing a display mode of a determined composition ratio. FIG. 16 is a diagram showing a display mode of a composition ratio in a case in which a user inputs "0" as a valence i of the first substance and "3" as a valence j of the second substance. In FIG. 16, the numerical value at the point where the valence i of the first substance is "0" and the valence j of the second substance is "3" is "5." Therefore, the controller 22 displays the area showing "5" on the display 24 in a more conspicuous manner than the other areas. By displaying in this manner, the user can recognize that the composition ratio of the first substance to the second substance is 1:5. Further, instead of or in addition to displaying the table shown in FIG. 16, the controller 22 may display an image of the composition ratio itself (e.g., an image of "1:5").

Further, in a case where "2" is input as the valence of the first substance and "4" is input as the valence of the second substance by the user, the controller 22 displays the area showing "0.33" in FIG. 16 on the display 24 in a more conspicuous manner than the other areas. By displaying in this manner, the user can recognize that the composition ratio of the first substance to the second substance is 1:0.33=3:1. As described above, the user can recognize the composition ratio.

[Modifications]

(1) In the embodiments described above, the description has been directed to the configuration in which the generation unit 340 generates the calibration curve based on the peak energy of the $K\alpha_1$ X-ray and the peak energy of the $K\alpha_2$ X-ray of a metal simple substance, the peak energy of the $K\alpha_1$ X-ray and the peak energy of the $K\alpha_2$ X-ray of each of the two or more compounds each containing the metal in their compositions, and the valence of the metal in each of the two or more compounds. However, the generation unit 304 may generate the calibration curve based on a plurality of types of peak energies (e.g., the peak energy of the $K\beta_{1,3}$ X-ray and the peak energy of the $K\alpha_2$ X-ray) based on the transitions of electrons of a metal contained in a sample irradiated with excitation ray, a plurality of types of peak energies of a metal simple substance, a plurality of types of peak energies of each of two or more types of compounds including a metal, and the valence of the metal in each of two or more types of compounds. When such a configuration is adopted, the analysis device acquires a plurality of types of peak energies (e.g., the peak energy of the $K\beta_{1,3}$ X-ray and the peak energy of the $K\alpha_2$ X-ray) of a metal contained in an unknown sample. The analysis device may calculate the mean valence of the metal contained in the unknown sample by applying the acquired plural types of peak energies to the calibration curve.

(2) In the embodiment described above, an example of a configuration has been described in which the parameter substituted for x of y=px+q, which is a calibration curve, is $K\alpha_1 - n \cdot K\alpha_2$. However, this parameter may be another parameter as long as it is defined by two types of peak energies. For example, it may be a $n \cdot K\alpha_1 - K\alpha_2$, or the like.

[Aspects]

It will be understood by those skilled in the art that the plurality of exemplary embodiments described above is illustrative of the following aspects.

(Item 1)

An X-ray analysis device according to one aspect of the present invention, includes:
- a device body provided with a spectrometer, the spectrometer being configured to detect intensity of characteristic X-rays for each wavelength by dispersing the characteristic X-rays generated by a sample irradiated with excitation ray; and
- a signal processing device configured to process a signal output from the device body, wherein the signal processing device includes:
- a storage unit configured to store a calibration curve, the calibration curve being generated based on
  - a peak energy of $K\alpha_1$ X-ray and a peak energy of $K\alpha_2$ X-ray emitted from a metal simple substance,
  - each of a peak energy of $K\alpha_1$ X-ray and a peak energy of $K\alpha_2$ X-ray emitted from two or more types of compounds each containing the metal in their compositions, the compounds being different in a valence of the metal, and a valence of the metal in each of the two or more types of compounds; and
- an operation unit configured to acquire a peak energy of the $K\alpha_1$ X-ray emitted from the metal contained in an unknown sample and a peak energy of the $K\alpha_2$ X-ray emitted from the metal based on intensity of the peak energy for each wavelength detected by the device body, and calculate a mean valence of the metal contained in the unknown sample by applying the acquired peak energy of the $K\alpha_1$ X-ray and the acquired peak energy of the $K\alpha_2$ X-ray to the calibration curve.

According to the X-ray analysis device of the above-described item 1, it is possible to improve the calculation accuracy of the mean valence of the metal in the sample.

(Item 2)

In the X-ray analysis device as recited in the above-described item 1,
- the calibration curve is represented by y=px+q,
  where y is a variable showing the mean valence, and x is a parameter obtained by subtracting a value obtained by multiplying the peak energy of the $K\alpha_2$ X-ray emitted from the metal by a coefficient n from the peak energy of the $K\alpha_1$ X-ray emitted from the metal, and
- the signal processing device generates the calibration curve by calculating a slope p, an intercept q, and a coefficient n, based on the peak energy of $K\alpha_1$ X-ray and the peak energy of $K\alpha_2$ X-ray emitted from the metal simple substance, the peak energy of $K\alpha_1$ X-ray and the peak energy of $K\alpha_2$ X-ray emitted from the metal contained in each of the two or more types of compounds, and the valence of the metal contained in each of the two or more types of compounds.

According to X-ray analysis device recited in the above-described item 2, the amount of operation for generating the calibration curve can be reduced as compared with an analytical measure for generating a complicated calibration curve.

(Item 3)

In the X-ray analysis device as recited in the above-described item 2, the signal processing device displays the calibration curve in which an X-axis represents a parameter and a Y-axis represents the mean valence on a display unit.

According to the X-ray analysis device recited in the above-described item 3, the user can grasp the used calibration curve by displaying the calibration curve used for the calculation of the mean valence.

(Item 4)

In the X-ray analysis device as recited in the above-described item 2 or 3,
- the two or more compounds include three or more types of compounds different from each other in the valence of the metal, and
- the signal processing device generates the calibration curve by calculating the slope p, the intercept q, and the coefficient n by applying the least-squares method to the peak energy of the $K\alpha_1$ X-ray and the peak energy of the $K\alpha_2$ X-ray emitted from the metal simple substance, the peak energy of the $K\alpha_1$ X-ray and the peak energy of the $K\alpha_2$ X-ray emitted from each of the metals of the three or more types of compounds, and the valence of the metal contained in each of the three or more types of compounds.

According to the X-ray analysis device recited in the above-described item 4, it is possible to generate a calibration curve reflecting the peak energy of the $K\alpha_1$ X-ray, the peak energy of the $K\alpha_2$ X-ray of a metal simple substance, the peak energy of the $K\alpha_1$ X-ray, and the peak energy of the $K\alpha_2$ X-ray of the metal of each of the three or more types of compounds, and the valence of the metal contained in each of the three or more types of compounds.

(Item 5)

In the X-ray analysis device as recited in the above-described item 2 or 3,
the two or more types of compounds contains a first compound and a second compound different from each other in the valence of the metal, and
the signal processing device generates the calibration curve by calculating the slope p, the intercept q, and the coefficient n using a following formula:

$$n=\{(v-w)\cdot m1 - v\cdot b1 + w\cdot a1\}/\{(v-w)\cdot m2 - v\cdot b2 + w\cdot a2\}$$

$$p=(v-w)/\{(a1-b1)-n\cdot(a2-b2)\}$$

$$q=\{w\cdot(a1-n\cdot a2)-v\cdot(b1-n\cdot b2)/\{(a1-a2)-n\cdot(a2-b2)\}$$

where m1 is the peak energy of the $K\alpha_1$ X-ray emitted from the metal simple substance,
m2 is the peak energy of the $K\alpha_2$ X-ray emitted from the metal simple substance,
v is the valence of the metal contained in the first compound,
w is the valence of the metal contained in the second compound,
a1 is the peak energy of the $K\alpha_1$ X-ray emitted from the first compound,
a2 is the peak energy of the $K\alpha_2$ X-ray emitted from the first compound,
b1 is the peak energy of the $K\alpha_1$ X-ray emitted from the second compound, and
b2 is the peak energy of the $K\alpha_2$ X-ray emitted from the second compound.

According to the X-ray analysis device recited in the above-described item 5, the calibration curve can be generated by a relatively simple calculation.

(Item 6)

In the X-ray analysis device as recited in any one of the above-described items 1 to 5,
the unknown sample is composed of a first substance and a second substance different from each other in the valence of the metal, and
the signal processing device outputs all possible composition ratios of the first substance and the second substance based on the calculated mean valence.

According to the X-ray analysis device recited in the above-described item 6, it is possible for the user to recognize all of composition ratios that can be taken by the first substance and the second substance (Item 7)

In the X-ray analysis device as recited in the above-described item 6,
the signal processing device
accepts inputs of the valence of the metal contained in the first substance and the valence of the metal contained in the second substance, and outputs a composition ratio of the first substance to the second substance based on the valence of the metal contained in the first substance, the valence of the metal contained in the second substance, and the mean valence.

According to the X-ray analysis device recited in the above-described item 7, the user can recognize the composition ratio between the first substance and the second substance.

(Item 8)

In the X-ray analysis device as recited in the above-described item 7,
the signal processing device calculates the composition ratio of the first substance to the second substance, based on 1:(ym−i)/(j−ym), wherein i<ym<j,
where, i is the valence of the metal contained in the first substance,
j is the valence of the metal contained in the second substance, and
ym is the calculated mean valence.

According to the X-ray analysis device recited in the above-described item 8, it is possible to calculate the composition ratio between the first substance and the second substance by a relatively simple operation.

(Item 9)

An X-ray analysis device according to another aspect of the present invention, includes:
a device body provided with a spectrometer, the spectrometer being configured to detect intensity of characteristic X-rays for each wavelength by dispersing the characteristic X-rays generated by a sample irradiated with an excitation ray; and
a signal processing device configured to process a signal output from the device body,
wherein the signal processing device is provided with
a storage unit configured to store a calibration curve generated based on a plurality of types of peak energies emitted from a metal simple substance, a plurality of types of peak energies emitted from two or more types of compounds each containing the metal in their compositions and having valences different from each other in the valence of the metal, and a valence of the metal in each of the two or more types of compounds, and
an operation unit configured to acquire a plurality of types of peak energies of the metal contained in an unknown sample, based on intensity for each wavelength detected by the device body, and calculate a mean valence of the metal contained in the unknown sample by applying the acquired plurality of types of peak energies to the calibration curve.

According to the X-ray analysis device recited in the above-described item 9, it is possible to improve the calculation accuracy of the mean valence of the metal in the sample.

(Item 10)

An X-ray analysis method according to still another aspect of the present invention, includes:
a step of acquiring a peak energy of $K\alpha_1$ X-ray emitted form a metal contained in an unknown sample and a peak energy of $K\alpha_2$ X-ray emitted from the metal by detecting intensity for each wavelength by dispersing characteristic X-rays generated from the unknown sample by emitting excitation ray to the unknown sample; and
a step of calculating a mean valence of the metal contained in the unknown sample by applying the acquired peak energy of the $K\alpha_1$ X-ray and the acquired peak energy of the $K\alpha_2$ X-ray to a calibration curve generated based on the peak energy of the $K\alpha_1$ X-ray and the peak energy of the $K\alpha_2$ X-ray emitted from the metal, each of the peak energy of the $K\alpha_1$ X-ray and the peak energy of the $K\alpha_2$ X-ray output from two or more types of compounds each containing the metal in their compositions and having valences different from each other in the valence of the metal, and a valence of the metal in each of the two or more types of compounds.

According to the analysis method recited in the above-described item 10 it is possible to improve the calculation accuracy of the mean valence of the metal in the sample.

The embodiments disclosed herein are to be considered in all respects as illustrative and not restrictive. The scope of the present invention is indicated by the appended claims rather than by the above-described foregoing descriptions and is intended to include all modifications within the meanings and ranges equivalent to the scope of the claims.

Description of Symbols

10: Device body
20: Signal processing device,
22: Controller
24: Display
26: Operation unit
30: Processor
32: Memory
100: Analysis device
110: Sample holder
120: Excitation source
130: Slit
140: Dispersive crystal
150: Detector
170: Charging and discharging device
302: Processing unit
304: Generation unit
306: Storage unit
308: Calculation unit

The invention claimed is:

1. An X-ray analysis device comprising:
a device body including a spectrometer, the spectrometer being configured to detect an intensity of characteristic X-rays by dispersing the characteristic X-rays generated by a sample irradiated with an excitation ray; and
a signal processing device including a controller configured to process a signal output from the spectrometer,
wherein the controller includes a storage unit configured to store a calibration curve, the calibration curve being generated based on:
a peak energy of $K\alpha_1$ X-rays and a peak energy of $K\alpha_2$ X-rays emitted from a metal as formed as a metal simple substance,
each of a peak energy of $K\alpha_1$ X-rays and a peak energy of $K\alpha_2$ X-rays emitted from two or more types of compounds, each compound containing the metal in its composition, each of the two or more types of compounds being different in a valence of the metal, and
a valence of the metal as contained in each of the two or more types of compounds, and
wherein the controller is configured to acquire a peak energy of the $K\alpha_1$ X-rays and acquire a peak energy of the $K\alpha_2$ X-rays emitted from the metal as contained in an unknown sample based on an intensity for each wavelength detected by the spectrometer, and configured to calculate a mean valence of the metal as contained in the unknown sample by applying the acquired peak energy of the $K\alpha_1$ X-rays and the acquired peak energy of the $K\alpha_2$ X-rays to the calibration curve.

2. The X-ray analysis device as recited in claim 1,
wherein the calibration curve is represented by $y=px+q$,
where y is a variable showing the mean valence of the metal as contained in the unknown sample, and x is a parameter obtained by subtracting a value obtained by multiplying the peak energy of the $K\alpha_2$ X-rays emitted from the metal by a coefficient n from the peak energy of the $K\alpha_1$ X-rays emitted from the metal, and
wherein the controller generates the calibration curve by calculating a slope p, an intercept q, and a coefficient n, based on the peak energy of the $K\alpha_1$ X-rays and the peak energy of the $K\alpha_2$ X-rays emitted from the metal as formed as the metal simple substance, the peak energy of the $K\alpha_1$ X-rays and the peak energy of the $K\alpha_2$ X-rays emitted from the metal as contained in each of the two or more types of compounds, and the valence of the metal as contained in each of the two or more types of compounds.

3. The X-ray analysis device as recited in claim 2,
wherein the signal processing device comprises a display, and the signal processing device is configured to display the calibration curve in which an X-axis represents a parameter and a Y-axis represents the mean valence of the metal as contained in the unknown sample on the display.

4. The X-ray analysis device as recited in claim 2,
wherein the two or more types of compounds include three or more types of compounds different from each other in the valence of the metal, and
wherein the controller generates the calibration curve by calculating the slope p, the intercept q, and the coefficient n by applying a least-squares method to the peak energy of the $K\alpha_1$ X-rays and the peak energy of the $K\alpha_2$ X-rays emitted from the metal as formed as the simple substance, the peak energy of the $K\alpha_1$ X-rays and the peak energy of the $K\alpha_2$ X-rays emitted from the metal as contained in each of the three or more types of compounds, and the valence of the metal as contained in each of the three or more types of compounds.

5. The X-ray analysis device as recited in claim 2,
wherein the two or more types of compounds contains a first compound and a second compound different from each other in the valence of the metal, and
wherein the controller generates the calibration curve by calculating the slope p, the intercept q, and the coefficient n using the following formula:

$$n=\{(v-w)\cdot m1-v\cdot b1+w\cdot a1\}/\{(v-w)\cdot m2-v\cdot b2+w\cdot a2\}$$

$$p=(v-w)/\{(a1-b1)-n\cdot(a2-b2)\}$$

$$q=\{w\cdot(a1-n\cdot a2)-v\cdot(b1-n\cdot b2)/\{(a1-a2)-n\cdot(a2-b2)\}$$

where m1 is the peak energy of the $K\alpha_1$ X-rays emitted from the metal as formed as the metal simple substance,
m2 is the peak energy of the $K\alpha_2$ X-rays emitted from the metal as formed as the metal simple substance,
v is the valence of the metal as contained in the first compound,
w is the valence of the metal as contained in the second compound,
a1 is the peak energy of the $K\alpha_1$ X-rays emitted from the first compound, a2 is the peak energy of the $K\alpha_2$ X-rays emitted from the first compound, b1 is the peak energy of the $K\alpha_1$ X-rays emitted from the second compound, and b2 is the peak energy of the $K\alpha_2$ X-rays emitted from the second compound.

6. The X-ray analysis device as recited in claim 1, wherein the unknown sample is composed of a first substance and a second substance different from each other in the valence of the metal, and wherein the signal processing device outputs several possible composition ratios of the first substance and the second substance based on the calculated mean valence of the metal as contained in the unknown sample.

7. The X-ray analysis device as recited in claim 6, wherein the signal processing device:
  is configured to accept inputs of the valence of the metal as contained in the first substance and the valence of the metal as contained in the second substance, and
  is configured to output a composition ratio of the first substance to the second substance based on the valence of the metal as contained in the first substance, the valence of the metal as contained in the second substance, and the mean valence of the metal as contained in the unknown sample.

8. The X-ray analysis device as recited in claim 7, wherein the controller is configured to calculate the composition ratio of the first substance to the second substance, based on 1:(ym−i)/(j−ym), wherein i<ym<j, where, i is the valence of the metal as contained in the first substance, j is the valence of the metal as contained in the second substance, and ym is the calculated mean valence of the metal as contained in the unknown sample.

9. An X-ray analysis device comprising:

a device body including a spectrometer, the spectrometer being configured to detect an intensity of characteristic X-rays by dispersing the characteristic X-rays generated by a sample irradiated with an excitation ray; and a signal processing device including a controller configured to process a signal output from the spectrometer, wherein the controller includes a storage unit configured to store a calibration curve generated based on a plurality of types of peak energies emitted from a metal as formed as a metal simple substance, a plurality of types of peak energies emitted from two or more types of compounds, each of the two or more types of compounds containing the metal in its composition and having a valence of the metal that is different from the others, and the valence of the metal as contained in each of the two or more types of compounds, and wherein the controller is configured to acquire a plurality of types of peak energies of the metal as contained in an unknown sample, based on an intensity for each wavelength detected by the spectrometer, and configured to calculate a mean valence of the metal as contained in the unknown sample by applying the acquired plurality of types of peak energies of the metal as contained in the unknown sample to the calibration curve.

10. An X-ray analysis method, comprising:

acquiring a peak energy of $K\alpha_1$ X-rays and acquiring a peak energy of $K\alpha_2$ X-rays emitted from a metal as contained in an unknown sample by dispersing characteristic X-rays generated from the unknown sample upon irradiating an excitation ray onto the unknown sample; and calculating a mean valence of the metal as contained in the unknown sample by applying the acquired peak energy of the $K\alpha_1$ X-rays and the acquired peak energy of the $K\alpha_2$ X-rays emitted from the metal as contained in the unknown sample to a calibration curve generated based on (a) a peak energy of $K\alpha_1$ X-rays and a peak energy of the $K\alpha_2$ X-rays emitted from the metal as formed as a metal simple substance, (b) for each of two or more types of compounds that contains the metal in its composition and has a valence of the metal that is different from the others, a peak energy of $K\alpha_1$ X-rays and a peak energy of $K\alpha_2$ X-rays emitted from the metal as contained in the corresponding type of compound, and (c) a valence of the metal as contained in each of the two or more types of compounds.

11. The X-ray analysis method of claim 10, further comprising identifying at least one possible composition of a substance of the unknown sample based on the calculated mean valence of the metal as contained in the unknown sample.

\* \* \* \* \*